(12) United States Patent
Matama

(10) Patent No.: US 7,061,000 B2
(45) Date of Patent: Jun. 13, 2006

(54) IMAGE PROCESSING APPARATUS FOR DETECTING AND CORRECTING DEFECTS

(75) Inventor: Toru Matama, Kanagawa (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 10/109,691

(22) Filed: Apr. 1, 2002

(65) Prior Publication Data

US 2002/0139943 A1 Oct. 3, 2002

(30) Foreign Application Priority Data

Mar. 30, 2001 (JP) .............................. 2001-101099

(51) Int. Cl.
*G01N 21/88* (2006.01)
*G06K 9/40* (2006.01)

(52) U.S. Cl. .................... 250/559.45; 250/559.02; 382/275

(58) Field of Classification Search ............... 250/330, 250/341.8, 226, 559.02, 559.4–559.46; 382/318, 382/275; 358/514; 356/237.1, 239.1
See application file for complete search history.

(56) References Cited

U.S. PATENT DOCUMENTS

| | | | |
|---|---|---|---|
| 5,266,805 A | 11/1993 | Edgar | 250/330 |
| 5,596,346 A * | 1/1997 | Leone et al. | 345/667 |
| 6,160,923 A * | 12/2000 | Lawton et al. | 382/275 |
| 6,233,364 B1 * | 5/2001 | Krainiouk et al. | 382/275 |
| 6,731,795 B1 * | 5/2004 | Ricard | 382/167 |
| 2003/0132384 A1 * | 7/2003 | Sugiyama et al. | 250/330 |

FOREIGN PATENT DOCUMENTS

| | | | |
|---|---|---|---|
| JP | 6 28468 A | | 2/1994 |
| JP | 2001-024884 | * | 1/2001 |
| JP | 2001-024895 | * | 1/2001 |

* cited by examiner

*Primary Examiner*—Thanh X. Luu
*Assistant Examiner*—Stephen Yam
(74) *Attorney, Agent, or Firm*—Birch, Stewart, Kolasch & Birch, LLP

(57) ABSTRACT

An image processing apparatus has an image reading unit which photoelectrically reads an image recorded on a film; a detecting unit which detects an image defect caused by a foreign particle deposited on the film and a flaw of the film using image data read with the image reading unit; a display unit which displays the image read with the image reading unit and the image defect detected by the detecting unit; an instruction unit which instructs at least one of the image defect to be processed automatically and the image defect to be processed manually; a processing unit which automatically processes the image defect that are instructed to be corrected automatically; and a correcting unit which manually corrects the remaining image defects.

9 Claims, 2 Drawing Sheets

IMAGE PROCESSING APPARATUS FOR DETECTING AND CORRECTING DEFECTS

BACKGROUND OF THE INVENTION

1. Filed of the Invention

The present invention relates to an image processing apparatus for processing image data obtained from an image recorded on a film, and more particularly to an image processing apparatus capable of preferably correcting image defects caused by a foreign particle deposited on the film and by a flaw of the film.

2. Related Background Art

Most of the images recorded on photographic films such as negatives and reversals (which are hereinafter referred to as "films") are conventionally printed onto light-sensitive materials (photographic papers) by a technique generally called "direct exposure" in which an image on a film is projected onto the light-sensitive material for areal exposure (one shot exposure).

In contrast, recently, an image recorded on a film is read photoelectronically to be converted into digital signals, which are subjected to various kinds of image processing to produce recording image data; and a light-sensitive material is exposed with recording light sensitive material is output as a print on which the image is recorded, and further the image data is also output to various recording mediums such as a CD-R, and a hard disk (HD) as an image file.

According to digital processing like this, since an image recorded on a film is read and subjected to image processing as digital image data, color and density can be very preferably corrected. In addition to the above, an image of high quality can be obtained by performing image processing such as gradation adjustment and sharpness processing (sharpness correction) which is basically impossible in a printer employing ordinary direct exposure.

Incidentally, when an image is output from a film acting as an original, an image defect is caused as a serious factor for deteriorated the quality of the image due to a foreign particle or matter such as dust and dirt deposited on the film, a flaw of the film formed by rubbing, and the like.

Conventional printers employing the direct exposure output a print by correcting the image defect of an image in such a manner that an operator manually cleans a film or corrects the image (film) with a color material. Whereas, in the digital processing in which an image of a film is read photoelectrically and processed as digital image data, it is possible to detect and correct an image defect by analyzing the image data obtained by reading the image.

For example, JP 6-28468 A discloses an image processing apparatus for correcting an image defect caused by a foreign particle and a flaw making use of infrared light (IR), which is not absorbed by an image recorded on a film but is shaded, absorbed and scattered by a foreign particle, a flaw, and the like. That is, in this image processing apparatus, when an image recorded on a film is photoelectrically read by a CCD sensor, or the like, the image is read with infrared light, in addition that visible images having three R (red), G (green), and B (blue) primary colors are read, so as to detect the foreign particle and the flaw by the change of intensity of the infrared light.

In image processing apparatuses including the image processing apparatus disclosed in the above publication for correcting an image defect caused by a foreign particle deposited on a film, a flaw thereof, and the like, the image defect is automatically corrected by the interpolation of image data, and the like, after the image defect is detected.

However, there are many case in which an image defect cannot be appropriately corrected depending upon a size of the image defect and a picture of the portion where the image defect is caused, and thus an unnatural image is created.

SUMMARY OF THE INVENTION

Accordingly, it is an object of the present invention for solving the problem of the conventional art to provide an image processing apparatus capable of appropriately correcting an image defect caused by a foreign particle such as dust, and the like deposited on a film and by a flaw, and the like of the film in image processing for photoelectrically reading an image recorded on the film and for correcting the image defect regardless of a size of the image defect and a picture at the position where the image defect is located.

In order to attain the above object, according to the present invention, it is provided that an image processing apparatus comprising: an image reading unit which photoelectrically reads an image recorded on a film; a detecting unit which detects an image defect caused by a foreign particle deposited on the film and a flaw of the film using image data read with the image reading unit; a display unit which displays the image read with the image reading unit and the image defect detected by the detecting unit; an instruction unit which instructs at least one of the image defect to be processed automatically and the image defect to be processed manually; a processing unit which automatically processes the image defect that are instructed to be corrected automatically; and a correcting unit which manually corrects the remaining image defects.

Preferably, the image reading unit reads the image recorded on the film as four-channel image data including R (red), G (green), and B (blue) visible image data and non-visible image data, and the detecting unit detects the image defect using the non-visible image data.

Preferably, the detecting unit, the display unit, the instruction unit, the processing unit, and the correcting unit perform processing when the image data output from the image reading unit is the four-channel image data.

Preferably, the image reading unit comprises an automatic image defect correcting unit as well as outputs image data together with a tag provided therewith that indicates whether or not an automatic image defect correction is carried out, and the detecting unit, the display unit, the instruction unit, the processing unit, and the correcting unit perform processing when image data provided with a tag indicating that the automatic image defect correction is not carried out is output.

DETAILED DESCRIPTION OF THE INVENTION

An image processing apparatus of the present invention will be described below in detail with reference to a preferable embodiment shown in the accompanying drawings.

Figure 1:
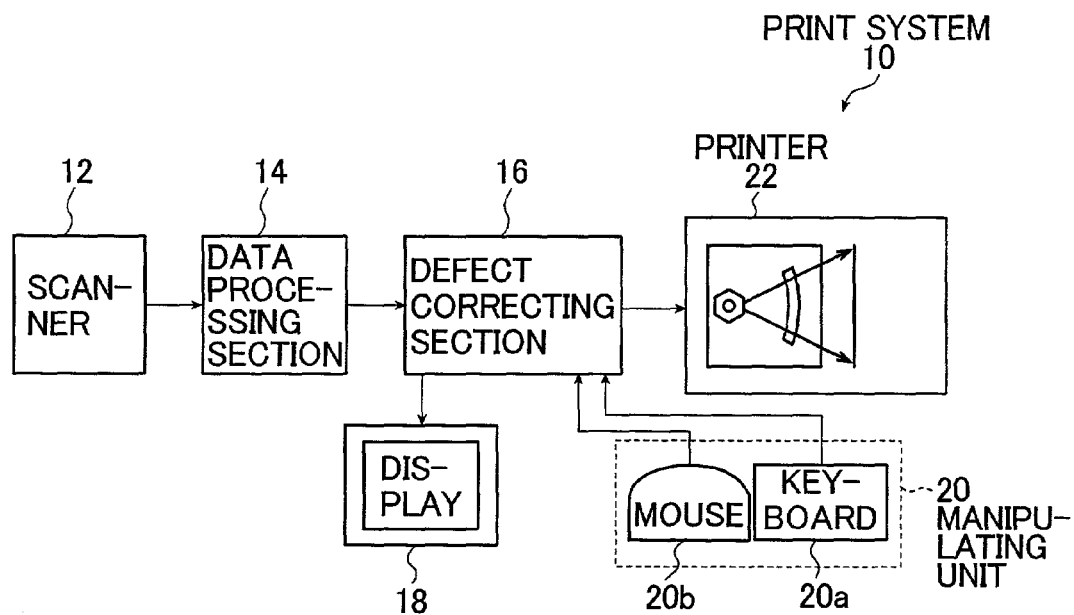
FIG. 1 is a block diagram of an embodiment of a print system making use of an image processing apparatus of the present invention.

FIG. 1 shows a block diagram of an embodiment of a print system using an image processing apparatus of the present invention.

The print system 10 shown in FIG. 1 reads an image recorded on a film F (shown in FIG. 2) photoelectrically and outputs the image as a print. The print system 10 is basically composed of a scanner 12, an data processing section 14, a defect correcting section 16, a display unit 18 connected to the defect correcting section 16, a manipulating unit 20 (a keyboard 20a and a mouse 20b), and a printer 22.

Figure 2:
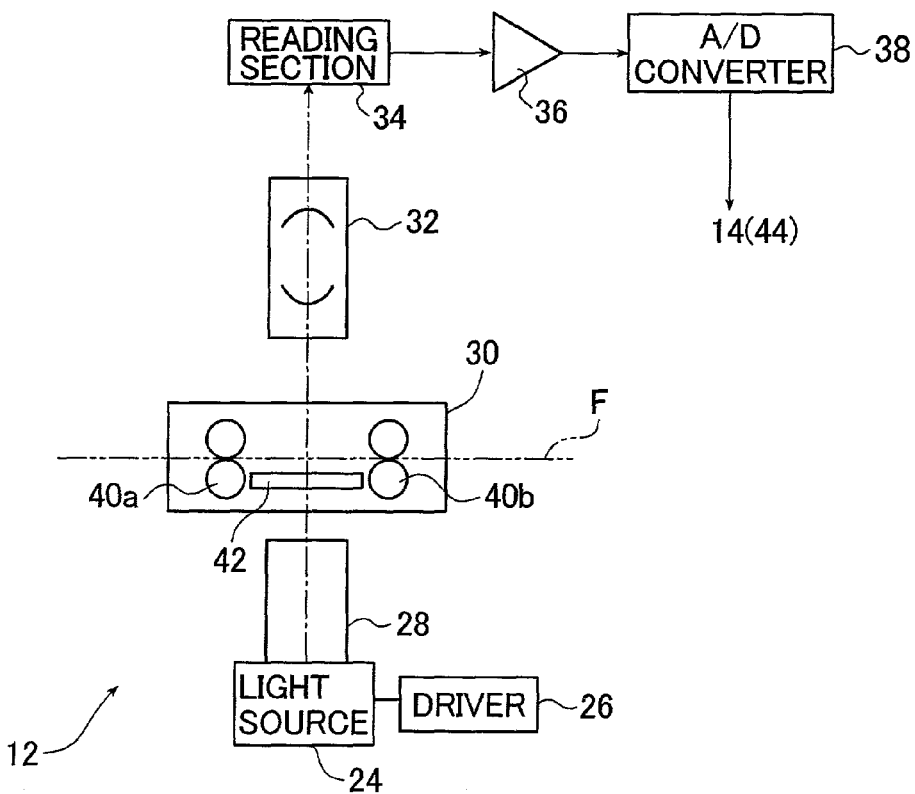
FIG. 2 is a conceptual view of a scanner of the print system shown in FIG. 1.

The scanner 12 is a device for photoelectrically reading the image recorded on the film F. As schematically shown in FIG. 2, the scanner 12 is composed of a light source 24, a driver 26, a diffusion box 28, a carrier 30, an imaging lens unit 32, a reading section 34, an amplifier 36, and an analog/digital (A/D) converter 38.

In the illustrated scanner 12, the light source 24 uses light emitting diodes (LEDs) and has three types of LEDs for emitting R (red) light, G (green) light, and B (blue) light as visible light, and an LED for emitting infrared light as invisible light. The light source 24 like this is driven by the driver 26 and sequentially emits the visible light and the infrared light.

The light emitted from the light source 24 is supplied to the diffusion box 28. The diffusion box 28 makes the light, which is incident on the film F, uniform in a film surface direction.

The carrier 30 intermittently transports the film F so as to transport and hold the respective images recorded on the film F (respective frames) to and at a predetermined reading position. A plurality of types of carriers are prepared according to a film size, and the like as the carrier 30 and are arranged so as to be touchably and detachably mounted on the main body of the scanner 12.

In the illustrated example, the carrier 30 has transport roller pairs 40a and 40b, which are disposed across a predetermined reading position to transport the film in a lengthwise direction, and a mask 42 for regulating the reading region of the image of each frame at the reading position. Further, the carrier 30 has a magnetic head, a barcode reader, and the like that are disposed thereon to read a magnetic recording medium (for Advanced Photo System) and bar codes such as a DX bar code, and the like.

The imaging lens unit 32 images the projecting light of the film F at the predetermined position of the reading section 34.

The reading section 34, which photoelectrically reads the film F using an area CCD sensor, reads the entire surface of one frame of the film F regulated by the mask 42 of the carrier 30 (reading of an image by areal exposure).

When the film F is read by the scanner 12 arranged as described above, first, the film F is transported by the carrier 30 so as to transport a frame to be read (ordinarily, first or final frame) to the reading position.

Next, the red LED, for example, of the light source 24 is driven by the driver 26 and emits red light. The red light is incident on the reading position so as to be incident on the frame held thereat after the quantity thereof is made uniform in the surface direction of the film F by the diffusion box 28, passes through the frame, and acts as projecting light for carrying the image recorded on the frame. This projecting light is imaged on the predetermined position (the light receiving surface of the area CCD sensor) of the reading section 34 by the imaging lens unit 32, and the red image of the frame is read photoelectrically.

Likewise, the green and blue images of the frame are read by sequentially emitting the green and blue LEDs of the light source 24, and finally the non-visible image of the frame is read with infrared light by emitting the infrared LED of the light source 24, thereby the reading of the frame is finished. Accordingly, the scanner 12 outputs four-channel image signals of the R (red), G (green) and B (blue) visible images and the infrared image (non-visible image).

When the image of one frame has been finished, the carrier 30 transports the film F so as to transport the image of a frame to be read next to the reading position.

The output signals from the reading section 34 is amplified by the amplifier 36, is converted into digital image signals by the A/D converter 38, and is supplied to the data processing section 14 (data correcting section 44).

In the print system 10, the scanner 12 reads the image recorded on one frame twice. That is, the scanner 12 carries out fine scan for reading the image at a high resolution to output a print, and the like and prescan for reading the image at a low resolution prior to the fine scan to determine the reading conditions of the fine scan and the image processing conditions in the data processing section 14.

At this time, the output signals in the prescan and the output signals in the fine scan are basically the same data except that they have a different resolution and a different output level.

In the image processing apparatus of the present invention, the scanner (image reading device) is by no means limited to the one using the area sensor and may be a scanner for reading an image by so-called slit scan using a four-line CCD sensor for reading an infrared image, in addition to red, green and blue images.

Figure 3:
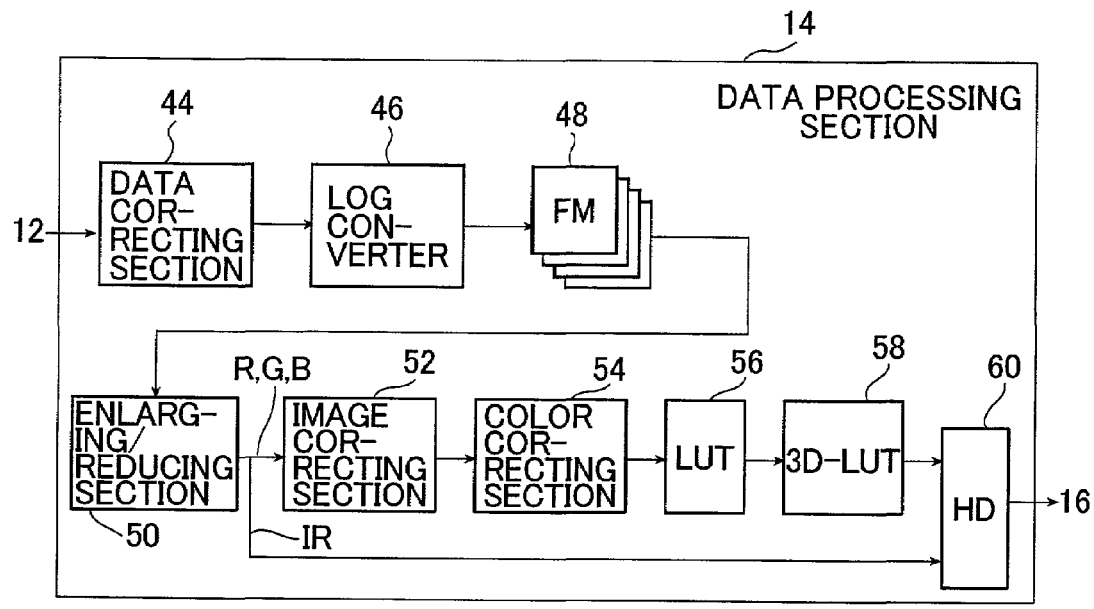
FIG. 3 is a block diagram of a data processing unit of the print system shown in FIG. 1.

As described above, the digital image signals output from the scanner 12 are supplied to the data processing section 14. FIG. 3 shows a block diagram of the data processing section 14.

As shown in FIG. 3, the data processing section 14 includes the data correcting section 44, a Log converter 46, frame memories 48, an enlarging/reducing section 50, an image correcting section 52, a color correcting section 54, a gradation converting section (look-up table) 56, a data converting section 58, and a hard disc 60.

Note that the data processing section 14 of the print system 10 may be branched downstream of the Log converter 46 (in the flow direction of data) and may include a processing path that includes components basically similar to the frame memories 48 to the data converting section 58 in order to display a simulation image used for a verification by processing the prescan data.

The data correcting section 44 is a section for subjecting the R, G, B, and IR image data output from the scanner 12 to predetermined corrections such as a DC offset correction, darkness correction, and shading correction.

The Log converter 46 subjects output data having been processed in the data processing section 44 to Log conversion through, for example, a look-up table (LUT) or the like and arranges it as a digital image (density) data.

Each of the R, G, B, and IR image data having been converted in the Log converter 46 is stored in each of the frame memories 48 that corresponds thereto.

The image data having been stored in the frame memories 48 is then subjected to enlargement/reduction processing (electronic magnification processing) in the enlarging/reducing section 50 so as to be arranged as image data having a size (number of pixels) corresponding to an output.

The infrared (IR) image data of the image data having been processed in the enlarging/reducing section 50 is supplied to the hard disc 60 as it is and stored in the position corresponding to the frame of the image data.

On the other hand, the image data of the R (red), G (green), and B (blue) visible images having been processed in the enlarging/reducing section 50 is then subjected to predetermined image processing such as sharpness processing in the image correcting section 52, and then is subjected to color correction (saturation correction) in the color correcting section 54 by a matrix, or the like.

The image data of the visible images having been processed in the color correcting section 54 is then subjected to a gradation conversion including a density correction and a color balance adjustment by a one-dimensional look-up table, or the like in the gradation converting section 56. When the film F is a negative film, negative image (density) data is converted into positive image (density) data, which corresponds to the output, by the gradation conversion.

The data converting section 58 converts the image data having been subjected to the gradation processing into image data corresponding to a print output using a three-dimensional (3D) look-up table, or the like. The image data of the thus converted R (red), G (green), and B (blue) visible images is supplied to the hard disc 60 and stored at the position corresponding to the frame of the images, similarly to the infrared (IR) image data.

That is, in the illustrated embodiment, a total of four-channel image data, that is, the image data of the three R (red), G (green), and B (blue) visible images and the image data of the IR (non-visible) image are stored in the hard disc 60. Alternatively, the four-channel image data may be stored in various types of a removable recording medium (removable memory) such as a CD-R and an MD.

Note that when no correction processing is carried out in the defect correcting section 16, which will be described later, the print system 10 may output a print by directly supplying the image data from the data converting section 58 to the printer 22 without supplying it to the hard disc 60. Alternatively, the print system 10 may arrange the image data having been processed in the data converting section 58 as an image file (digitize the image data) and may supply it to a recording medium such as a CD-R or may output both the print and the image file.

When no image defect is corrected in the print system 10, the scanner 12 needs not to read the infrared (IR) image.

The defect correcting section 16 is a section in which an image defect such as the white region as if the white color of the printing paper could be directly observed and the uneven stripe of an image is corrected which is caused by a foreign particle or matter such as dust and dirt deposited on the film F and by the damage thereof due to rubbing of it.

An ordinary image processing apparatus for correcting an image defect detects image defects using an infrared (IR) image and automatically corrects all the image defects by the interpolation, and the like of image data. However, the automatic correction using the interpolation, and the like cannot appropriately correct an image defect depending on a size of the image defect and on a picture at the position where the image defect exists. An example of the picture is, for example, a human eye that moves intensely, Thus, it is often the case that an image, which is corrected by the above ordinary apparatus, is unnatural and has a problem in its quality, as described above.

In contrast, the defect correcting section 16 of the print system 10 making use of the present invention interactively selects image defects that are to be automatically corrected and image defects that are to be manually corrected by the operator and corrects them. With this operation, the print system 10 can output an appropriately corrected image of high quality regardless of a size of an image defect and a picture at the position where the image defect exists.

The image processing apparatus of the present invention will be described below in more detail by explaining the overall operation of the defect correcting section 16.

When an image defect is corrected, the defect correcting section 16 reads out the four-channel (R, G, B, and IR) image data of a frame the image defect of the image of which is to be corrected from the hard disc 60 of the data processing section 14. First, the defect correcting section 16 detects the image data using the IR image data.

As known well, when the film F has a foreign particle or a flaw, both R, G, and B visible light and invisible light such as infrared light are absorbed, shaded, and scatted by the foreign particle or the flaw. Accordingly, when the foreign particle, or the like exists on the film F, the intensity of the projecting light of the film is reduced or increased, which impinges on the foreign particle, or the like and then is incident on the image sensor 34 (CCD sensor).

In contrast, as to an image (visible image) recorded on the film F, R (red), G (green), and B (blue) visible light is absorbed according to the image, and the intensity of the resultant projecting light is changed thereby. However, infrared (IR) light passes through the film F without being absorbed by the image at all. As a result, when no foreign particle or the like exist on the film F, the IR light basically has the same intensity over the entire surface of one frame (area CCD sensor), and IR image data is made uniform on all the pixels of the one frame.

Therefore, only when the film F has the foreign particle or the flaw, the intensity of the infrared light having passed through the film F, namely, image data is varied according to the foreign particle or the flaw.

The defect correcting section 16 makes use of this variation and detects the image defect using the infrared (IR) image data.

Note that the method of detecting the image defect (the foreign particle or the flaw of the film F) is not limited to the above method, and various known methods can be used.

Further, when the data processing section 14 outputs the image data to the removable storage such as the CD-R, as described above, the defect correcting section 16 may read out the four-channel image data therefrom.

Further, when the image data read from the hard disc 60 is not the four-channel image data described above but only the image data of the R (red), G (green), and B (blue) visible images, the defect correcting section 16 supplies the image data to the printer 22 without subjecting it to defect correction processing. Further, when the data processing section 14 has an automatic image defect correcting function, the image data supplied to the hard disc 60 may be provided with a tag indicating the presence or absence of automatic correction. In this case, the defect correcting section 16 may directly supplies image data, which has a tag indicating that the automatic correction is present, to the printer 22 without subjecting the image data to image defect correction.

Next, the defect correcting section 16 displays the R (red), G (green), and B (blue) image data on the display unit 18 as a visible image as well as also displays a result of detection of image defects thereon. As a method of displaying image defects, a detected image defect is displayed, for example, by color such as red that can be easily discriminated or is indicated by an arrow. When the image defect is displayed by color, the image of R (red), G (green), and B (blue) image data may be displayed in black and white so that the image defect can be easily discriminated.

Figure 4:
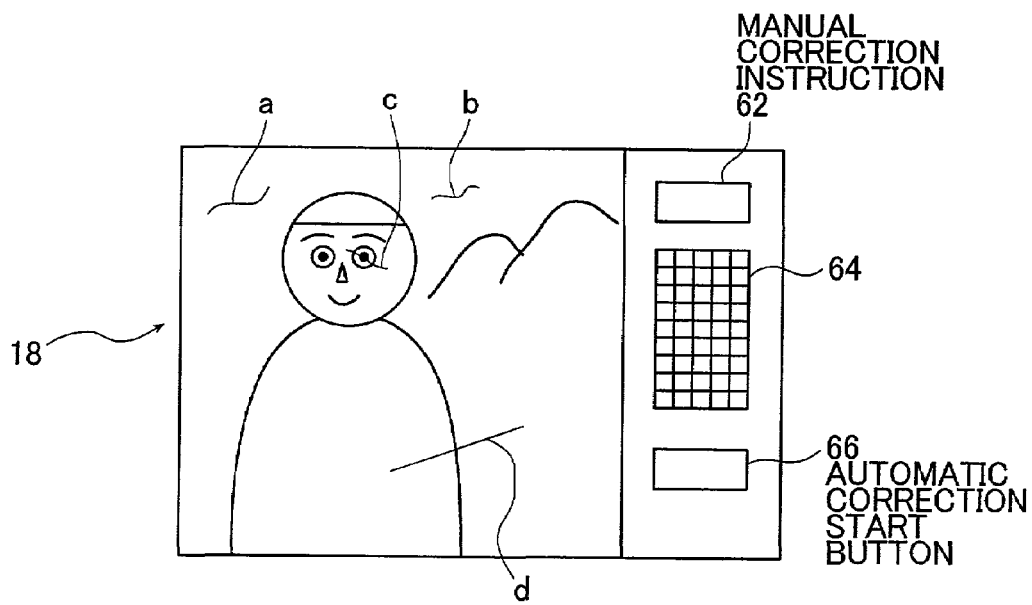
FIG. 4 is a view conceptually showing an example of a correction screen for correcting an image defect in the print system shown in FIG. 1.

FIG. 4 shows an example of a screen of the display unit 18.

In this example, an image is displayed on the left side of the screen, and processing tools (a manual correction instructing button 62, a retouch tool 64, and an automatic correction start button 66) making use of a graphical user interface (GUI) are displayed on the right side. In the illustrated example, it is assumed that four image defects "a", "b", "c" and "d" caused by foreign particles or flaws are detected.

As a method of displaying an image, the entire portion of the image of one frame may be displayed as in the illustrated example, or a part of the image may be displayed and the entire portion of the image may be confirmed by scrolling the image longitudinally and laterally or by changing over partial images.

When the image is displayed, the operator depresses the manual correction instructing button 62 (for example, clicks it with the mouse 20b), and then selects and inputs an image defect (for example, the image defect "c" located at the position of an eye) whose appropriate automatic correction by interpolation, or the like is determined difficult.

The selection and the input are carried out by a known method of indicating a region including an image defect or of designating (clicking) an image defect itself, using the graphical user interface (GUI). Further, the image defect that is indicated to be manually corrected may be displayed by changing its color or by surrounding it with a frame so that it can be easily discriminated.

When the operator designates all the image defects to be corrected manually, he or her depresses the automatic correction start button 66. With this operation, the automatic correction of the image defects "a", "b", and "d" in the figure other than the image defect whose manual correction is not designated, for example, the image defect "c" located at the position of an eye starts.

Note that, in this example, the image defect to be corrected manually is designated and the image defects other than it are automatically corrected. However, the present invention is by not means limited thereto, and the image defects to be corrected automatically may be selected inversely. Alternatively, both the image defect to be corrected manually and the image defects to be corrected automatically may be selected. Further, when an image defect is detected erroneously, an instruction for canceling the correction of it may be input.

The automatic image defect correction method is not particularly limited, and any known methods such as a method of making use of continuity of peripheral pixels, a method of correcting the pixels of an image defect (infilling blanks of the image defect) by interpolation using the image data of peripheral pixels. In addition to the above methods, the methods disclosed in various patent applications including JP 6-28468 A described above may be used.

When the image defects have been automatically corrected or simultaneously with the automatic correction of the image defects, the operator corrects the image defects whose manual correction has been selected in the image data of the R (red), G (green), and B (blue) visible images.

This image correction can be carried out using the retouch tool 64 in the same way as that performed using commercially available retouch software such as "Photoshop®" manufactured by Adobe systems incorporated., in for example, a personal computer, and the like. Otherwise, the image correction may be carried out in the defect correcting section 16 (print system 10) using commercially available retouch software.

When the image defects have been manually corrected, the operator issues an output instruction.

In response to the instruction (when the automatic correction has been also finished), the image data of the corrected R (red), G (green), and B (blue) visible images are supplied to the printer 22.

That is, according to the present invention, all the image defects can be appropriately corrected and an image of high quality without unnatural picture can be output while securing good workability by automatically correcting the image defects that can be automatically corrected by interpolation, and the like and by correcting the image defects whose automatic correction is difficult through the manual correction performed by the operator.

The printer 22 is a known color printer. There is exemplified a printer for outputting a photosensitive material such as a photographic paper, or the like as a print after the light-sensitive material is two-dimensionally scan exposed with, for example, a light (laser) beam, which is modulated according to R (red), G (green), and B (blue) image data supplied so as to record a latent image thereon, and after the thus exposed light-sensitive material is subjected to wet type development processing including development, fixing, and rinsing so that the latent image is converted to a visible image, and then is dried.

In the illustrated print system 10, the image data having been processed in the defect correcting section 16 may be arranged as an image file and may be output to a recording medium such as a CD-R in place of outputting it as a print.

As an example, when an image file of Joint Photographic Expert Group (JPEG) is output, first, the image data having been corrected in the defect correcting section 16 is converted by a three-dimensional look-up table, or the like and is arranged as image data corresponding to an image file to be output, that is, as, for example, image data of s-RGB standard. Next, the image data is JPEG-compressed by being processed using a quantization table and a Huffman table. Thereby the image data is arranged as base line image data of the JPEG format.

The image file is provided with a tag of Exchangeable Image File Format (Exif), when necessary, so that it is arranged as a so-called JPEG (Exif) format image file. The image file is added with a thumbnail image, when necessary, and is supplied to the recording medium such as the CD-R as the image file. Further, a tag indicating the presence or absence of an image defect correction may be added to the image file.

Note that the recording medium to which the image file is output is not particularly limited, and various types of known recording mediums such as an MO(Magnet Optical), a smart media™, an HiFD™, a Zip™, and a hard disc can be used. Further, the image file may be output to a communication network such as the Internet and to a personal computer, and the like that are connected to the print system 10 through an interface, in addition to the recording medium.

While the image processing apparatus of the present invention has been described above in detail, the present invention is by no means limited to the above embodiment and it goes without saying that various improvements and modifications can be made within the range which does not depart from the gist of the present invention.

For example, the data processing section 14 is arranged independently of the defect correcting section 16 in the illustrated print system 10. However, the present invention is by no means limited thereto and they may be arranged as a single integral unit in which the defect correcting section 16, for example, is assembled in the data processing section 14.

At this time, while an image defect may be corrected at any position from the scanner 12 to the printer 22, it is preferably corrected downstream of the enlarging/reducing section 50. When there is a possibility that an image defect is emphasized in sharpness processing, it is preferable that the image defect be corrected upstream of the image correcting section 52. At this time, the image data, which has been subjected to predetermined processing including the image defect correction, may be output to the printer 22 (recording medium) without disposing the hard disc downstream of the three-dimensional look-up table.

As described above in detail, according to the image processing apparatus of the present invention that photoelectrically reads an image recorded on a film and corrects an image defect caused by the flaws, and the like of the film, the image defects to be corrected automatically and the image defects to be corrected manually are interactively selected and corrected, respectively. Accordingly, the image processing apparatus can output an image of high quality by appropriately correcting all the image defects while securing good workability.

The invention claimed is:

1. An image processing apparatus comprising:
   an image reading unit which photoelectrically reads an image recorded on a film;
   an enlarging/reducing unit which subjects data of the read image to electronic magnification processing;
   a detecting unit which detects one or more image defects caused by at least one of a foreign particle deposited on the film and a flaw of the film using image data enlarged or reduced with the enlarging/reducing unit;
   a display unit which displays the image enlarged or reduced with the enlarging/reducing unit and the one or more image defects detected by the detecting unit;
   an instruction unit which allows to interactively select either one or more image defects to be processed automatically, or one or more image defects to be processed manually using a displayed image displayed on the display unit, and instructs interactively at least one of the one or more image defects to be processed automatically and the one or more image defects to be processed manually using a displayed image displayed on the display unit;
   a processing unit which automatically processes to correct the one or more image defects that are instructed to be corrected automatically;
   a correcting unit which manually corrects the remaining one or more image defects or the one or more image defects that are instructed to be corrected manually,
   wherein the instruction unit allows a user to optionally select between processing the image defects automatically or manually, and
   a data processing unit that subjects the image data read with the image reading unit to predetermined image processing;
   wherein the data processing unit has an automatic image defect correcting function as well as outputs image data together with a tag provided therewith that indicates whether or not an automatic image defect correction is carried out using the automatic image defect correcting function, and
   wherein the detecting unit, the display unit, the instruction unit, the processing unit, and the correcting unit perform image defect correction processing only when image data provided with a tag indicating that the automatic image defect correction is not carried out is output from the data processing unit.

2. The image processing apparatus according to claim 1, wherein the image reading unit reads the image recorded on the film as four-channel image data including R (red), G (green), and B (blue) visible image data and non-visible image data, and the detecting unit detects the one or more image defects using the non-visible image data.

3. The image processing apparatus according to claim 1, wherein the detecting unit, the display unit, the instruction unit, the processing unit, and the correcting unit perform image defect correction processing when the image data output from the image reading unit is the four-channel image data.

4. The image processing apparatus of claim 1, wherein the image data is manually corrected by the user on a pixel by pixel basis.

5. The image processing apparatus according to claim 1, further comprising an image correcting unit which subjects the enlarged or reduced image to sharpness processing, the sharpness processing performed after corrections of image defects by the processing unit and by the correcting unit so as to prevent the image defects from being emphasized.

6. The method according to claim 1, wherein the enlarged or reduced image data is subjected to sharpness processing after automatic correction and manual corrections of the image defects so as to prevent the image defects from being emphasized.

7. A method for processing image data comprising:
   photoelectrically reading an image recorded on a film;
   enlarging/reducing data of the read image;
   detecting one or more image defects caused by at least one of a foreign particle deposited on the film and a flaw of the film using image data read with the image reading unit and enlarged/reduced;
   displaying the read image based on the enlarged/reduced image data;
   enabling to interactively select either one or more image defects to be processed automatically, or one or more image defects to be processed manually using a displayed image displayed on the display unit, and instructing interactively at least one of the one or more image defects to be processed automatically and the one or more image defects to be processed manually using a displayed image displayed on the display unit;
   subjecting the image data read to predetermined image processing;
   outputting image data together with a tag provided therewith that indicates whether or not an automatic image defect correction is carved out using an automatic image defect correcting function, and
   automatically processing to correct the one or more image defects that are instructed to be corrected automatically by performing image defect correction processing only when image data provided with a tag indicating that the automatic image defect correction is not carried out is output from the data processing unit; and
   enabling manual correction of the remaining one or more image defects or the one or more image defects that are instructed to be corrected manually, wherein a user may optionally select between processing the image defects automatically or manually.

8. An image processing apparatus comprising:

an image reading unit which photoelectrically reads an image recorded on a film;

an enlarging/reducing unit which subjects data of the read image to electronic magnification processing;

a detecting unit which detects one or more image defects caused by at least one of a foreign particle deposited on the film and a flaw of the film using image data enlarged or reduced with the enlarging/reducing unit;

a display unit which displays the image enlarged or reduced with the enlarging/reduction unit and the one or more image defects detected by the detecting unit;

an instruction unit which allows to interactively select either one or more image defects to be processed automatically, or one or more image defects to be processed manually using a displayed image displayed on the display unit, and instructs interactively at least one of the one or more image defects to be processed automatically and the one or more image defects to be processed manually using a displayed image displayed on the display unit;

a processing unit which automatically processes to correct the one or more image defects that are instructed to be corrected automatically;

a correcting unit which manually corrects the remaining one or more image defects or the one or more image defects that are instructed to be corrected manually, wherein the instruction unit allows a user to optionally select between processing the image defects automatically or manually; and an image correcting unit which subjects the enlarged or reduced image to sharpness processing, the sharpness processing performed after corrections of image defects by the processing unit and by the correcting unit so as to prevent the image defects from being emphasized.

9. A method for processing image data comprising:

photoelectrically reading an image recorded on a film;

enlarging/reducing data of the read image;

detecting one or more image defects caused by at least one of a foreign particle deposited on the film and a flaw of the film using image data read with the image reading unit enlarged/reduced;

displaying the read image based on the enlarged/reduced image data;

enabling to interactively select either one or more image defects to be processed automatically, or one or more image defects to be processed manually using a displayed image displayed on the display unit, and instructing interactively at least one of the one or more image defects to be processed automatically and the one or more image defects to be processed manually using a displayed image displayed on the display unit;

automatically processing to correct the one or more image defects that are instructed to be corrected automatically; and enabling manual correction of the remaining one or more image defects or the one or more image defects that are instructed to be corrected manually, wherein a user may optionally select between processing the image defects automatically or manually, and wherein the enlarged or reduced image data is subjected to sharpness processing after automatical correction and manual corrections of the image defects so as to prevent the image defects from being emphasized.

* * * * *